United States Patent
Arai et al.

(10) Patent No.: US 8,025,638 B2
(45) Date of Patent: Sep. 27, 2011

(54) BALLOON CATHETER, MEDICAL APPARATUS AND METHOD FOR TREATING LIVING ORGAN

(75) Inventors: Tsunenori Arai, Ota-ku (JP); Atsushi Utsumi, Kawanishi (JP); Takashi Kawabata, Hasuda (JP)

(73) Assignees: Keio University, Tokyo (JP); Nipro Corporation, Osaka (JP)

( * ) Notice: Subject to any disclaimer, the term of this patent is extended or adjusted under 35 U.S.C. 154(b) by 1060 days.

(21) Appl. No.: 10/851,547

(22) Filed: May 21, 2004

(65) Prior Publication Data

US 2005/0261626 A1    Nov. 24, 2005

(51) Int. Cl.
*A61F 7/12* (2006.01)
*A61F 7/00* (2006.01)
*A61M 29/00* (2006.01)

(52) U.S. Cl. .................. 604/113; 604/96.01; 607/96

(58) Field of Classification Search .............. 604/96.01, 604/113; 607/96
See application file for complete search history.

(56) References Cited

U.S. PATENT DOCUMENTS

| | | | |
|---|---|---|---|
| 4,662,383 A | 5/1987 | Sogawa et al. | |
| 4,955,377 A | 9/1990 | Lennox et al. | |
| 5,151,100 A | 9/1992 | Abele et al. | |
| 5,191,883 A | 3/1993 | Lennox et al. | |
| 5,226,430 A | 7/1993 | Spears et al. | |
| 5,344,419 A | 9/1994 | Spears et al. | |
| 5,368,591 A | 11/1994 | Lennox et al. | |
| 5,417,689 A | 5/1995 | Fine | |
| 5,496,311 A | 3/1996 | Abele et al. | |
| 6,223,085 B1 | 4/2001 | Dann et al. | |
| 6,302,904 B1 | 10/2001 | Wallstén et al. | |
| 6,710,135 B2 * | 3/2004 | Tan et al. | 525/411 |
| 7,147,618 B2 * | 12/2006 | Kurz | 604/57 |
| 2002/0133081 A1 * | 9/2002 | Ackerman et al. | 600/486 |
| 2004/0021249 A1 * | 2/2004 | Weber et al. | 264/248 |

FOREIGN PATENT DOCUMENTS

| | | |
|---|---|---|
| JP | 61-113438 A | 5/1986 |
| JP | 4-117958 A | 4/1992 |
| JP | 5-177001 A | 7/1993 |

(Continued)

OTHER PUBLICATIONS

Interrogation dated Jul. 22, 2010 in corresponding Japanese Patent Application No. 2003-434588 and an English-language translation thereof.

(Continued)

*Primary Examiner* — Nicholas D Lucchesi
*Assistant Examiner* — Victoria P Campbell
(74) *Attorney, Agent, or Firm* — Holtz, Holtz, Goodman & Chick, PC

(57) ABSTRACT

A balloon catheter including a connecting member, a catheter shaft, a balloon and a heat-generating member. The heat-generating member is in contact with a fluid in a distal portion of the catheter shaft. A method for treating a patient including introducing a low temperature fluid which flows through the balloon, introducing energy into a catheter shaft, and converting the energy into heat by a heat-generating member to heat the fluid, whereby an organ of the patient is heated and cooled. In the method, a portion of a diseased tissue of the organ is (i) heated from 35 to 40° C. to 60 to 80° C. within 30 seconds, (ii) expanded by applying a pressure of 500 kPa or smaller to the balloon, and (iii) cooled to 45° C. or lower within 40 seconds.

19 Claims, 4 Drawing Sheets

FOREIGN PATENT DOCUMENTS

| | | |
|---|---|---|
| JP | 05-212118 A | 8/1993 |
| JP | 6-510450 A | 11/1994 |
| JP | 07-213621 A | 8/1995 |
| JP | 08-98857 A | 4/1996 |
| JP | 2535250 B2 | 6/1996 |
| JP | 2864094 B2 | 12/1998 |
| JP | 2984056 B1 | 9/1999 |
| JP | 2002-301087 A | 10/2002 |
| JP | 2002-331034 A | 11/2002 |
| JP | 2003-220068 A | 8/2003 |
| WO | WO 91/03207 A1 | 3/1991 |
| WO | WO 93/04727 A1 | 3/1993 |

OTHER PUBLICATIONS

Partial English-language translation and an English-language computer translation of JP 2002-331034.

\* cited by examiner

BALLOON CATHETER, MEDICAL APPARATUS AND METHOD FOR TREATING LIVING ORGAN

BACKGROUND OF THE INVENTION

1. Field of the Invention

The present invention relates to a balloon catheter, a medical apparatus, a method for treating a living organ and a use of the medical apparatus for treating a living organ. More particularly, the present invention relates to a balloon catheter which can cure a diseased tissue by heating and cooling a living organ in a very short time and, in particular, can expand a blood vessel without causing damages when the balloon catheter is used in the percutanuous transluminal coronary angioplasty, a medical apparatus comprising the balloon catheter, a method for treating a living organ using the balloon catheter and a use of the medical apparatus for treating a living organ.

2. Description of Related Art

The percutanuous transluminal coronary angioplasty (PTCA) using a balloon is being widely conducted recently. In the period shortly after the introduction of the technology, examples of the operation in which PTCA was applied and the diseases to which PTCA could be applied were rather limited. Due to the progress in instruments and technology, the application of this technology has been expanded not only to multivessel diseases but also to complete occlusion and acute myocardial infarction. However, the frequency of recurrence of stenosis is great, and this is considered to be the greatest problem of PTCA. To prevent the recurrence of stenosis, various stents have been developed and used. However, the effect of preventing the recurrence of stenosis is limited, and the presence of the remaining stent occasionally works as an obstacle for the treatment. Moreover, stainless steel used as the material of the stent occasionally exhibits allergic effects to the tissue. Therefore, it has been desired that stenosis is treated without using a foreign substance such as stainless steel and the recurrence of stenosis is prevented. Heretofore, it has been tried that a tissue of a tubular organ is burned or vaporized directly by a laser treatment or that the portion of stenosis is treated with argon laser beams. However, these trials failed without significant effects due to formation of serious damages to tissues or adverse effects of decomposition products.

It is considered that, when a cell of a smooth muscle is damaged and the tissue is restored by the stem cell, abnormal information due to the damage is transferred or abnormal division of a stem cell takes place, and the recurrence of stenosis of a tubular organ takes place. It is occasionally conducted that a blood vessel for the treatment is cut by a so-called transluminal extraction catheter (TEC) or a rotablator so that the outer membrane alone is left remaining, and a stent is disposed thereafter. When a necessary tissue is removed by the cutting, the tissue of the inner skin is not stabilized even when the tissue is formed, and this is considered to cause the recurrence of stenosis. Since a blood vessel is forced to expand by a pressure as great as 800 to 1,000 kPa in the ordinary PTCA, the tissue is torn or the tissue of the blood vessel is degraded by the great force. Therefore, the recurrence of stenosis tends to take place due to excessive growth of the cells of the smooth muscle during the restoration of the coronary artery.

The development of instruments and methods for expanding a blood vessel without causing damages to the blood vessel at the portion of stenosis have been conducted. For example, as the apparatus useful for applying heat to the inside of the body of a patient in a treatment such as the treatment for forming blood vessels, a system for expanding a tubular organ in the body having a means for controlling a catheter which applies heat and pressure to a tissue of a tubular organ simultaneously, detects the change in the behavior of yielding or the change in the thermal conductivity of the tissue of the tubular organ, and react to the behavior of the tissue, is proposed (Japanese Patent No. 2984056, page 2). However, it is very difficult that the physiological reaction of a portion of disease in a very different diseased condition in each case is examined under a single criterion and the most suitable treatment is applied to the portion of disease. In PTCA, as the catheter which can solidify the inner face of a blood vessel by heating to prevent recurrence of stenosis without causing damages on the inner membrane of the blood vessel, a catheter equipped with a balloon made of a fluororesin and having a heating tube absorbing laser beams and a laser fiber protruding into the balloon, is proposed (Japanese Patent No. 2535250. pages 1 and 2). However, the thickness of the blood vessel tends to decrease when the inner wall of the blood vessel is heated at 80 to 90° C. As the catheter which prevents excessive local heating of the inside of the balloon, a catheter which has a heating tube having a metal braid and a resin tube covering the metal braid and two thermocouples in the balloon, is proposed (Japanese Patent No. 2864094, pages 1 and 2). However, this catheter has a problem in that it is difficult that a excellent result is obtained with stability when an excessively great force or an excessively great invasion of heat is applied to a blood vessel.

SUMMARY OF THE INVENTION

The present invention has an object of providing a balloon catheter, a medical apparatus, a method for treating a living organ and a use of the medical apparatus for treating a living organ which can heat and cool the living organ within a very short time to cure a diseased tissue and expand a blood vessel without damages, in particular, in application to the percutanuous transluminal coronary angioplasty.

As the result of intensive studies by the present inventors to overcome the above problems, it was found that a blood vessel could be expanded without damages by using a medical apparatus equipped with a means for heating a balloon to 80° C. in a short time and a means for cooling the balloon to 45° C. in a short time. The present invention has been completed based on this knowledge.

The present invention provides:

(1) A balloon catheter which comprises a proximally disposed connecting member comprising an inlet for a fluid, an outlet for a fluid and an inlet for energy, a balloon, a catheter shaft comprising a lumen for introducing the fluid into the balloon and a lumen for discharging the fluid from the balloon and a heat-generating member, wherein the proximally disposed connecting member and a proximal portion of the catheter shaft are connected to each other, a distal portion of the catheter shaft and a proximal portion of the balloon is connected to each other, and the heat-generating member is in contact with the fluid at an inside of the balloon or in a distal portion of the catheter shaft;

(2) A balloon catheter according to (1), wherein the balloon comprises a thermoplastic resin and is prepared in accordance with a blow molding process at a temperature of 100° C. or higher, and the heat-generating member is in contact with the fluid in the distal portion of the catheter shaft;

(3) A medical apparatus which comprises a balloon catheter described in any one of (1) and (2) and a temperature sensor disposed at an inside of the balloon or at the catheter shaft at a distal position from the position of the heat-generating member, wherein the fluid at a low temperature is introduced from the inlet for a fluid, flows through an inside of the balloon and is discharged from the outlet for a fluid, energy is introduced from the inlet for energy into the catheter shaft, is converted into heat by the heat-generating member and heats the fluid, and a living organ is heated and cooled for a medical treatment by the balloon which is heated and cooled, respectively, with the fluid;

(4) A medical apparatus according to (3), which has an ability of heating the balloon from 35~40° C. to 60~80° C. within 30 seconds and cooling from the temperature attained by the heating to a temperature of 45° C. or lower within 40 seconds;

(5) A medical apparatus according to (3), wherein the apparatus comprises a means for detecting a pressure, and the balloon is expanded by applying a pressure with adjustment of degrees of opening of the inlet for a fluid and the outlet for a fluid or a pressure of the introduced fluid;

(6) A medical apparatus according to (3), wherein the energy is laser beams, which are introduced into the catheter shaft from the inlet for energy via an optical fiber, and a tip portion of the optical fiber has a cone shape having a diameter gradually decreasing towards the tip;

(7) A method for treating a living organ which comprises, providing the medical apparatus described in (3), inserting the catheter of said apparatus into a living organ to be treated to make the balloon of said catheter reach a portion of disease, introducing the fluid at low temperature into the balloon, supplying energy to the heat-generating member during a time to effect the portion of disease is heated to a temperature level which is effective for the treatment of the portion of disease and is lower than the temperature at which the living organ is undesirably damaged, cutting off the energy, and cooling the portion of disease below the temperature at which the living organ is not damaged;

(8) A method for treating a living organ which comprises, using a medical apparatus described in any one of (3), (4), (5) and (6), heating a portion of disease of the living organ from 35~40° C. to 60~80° C. within 30 seconds, expanding the portion of disease by applying a pressure of 500 kPa or smaller to the balloon, and cooling the portion of disease from the temperature attained by the heating to a temperature of 45° C. or lower within 40 seconds;

(9) A method for treating a living organ according to (7), wherein a portion of disease of a blood vessel is heated from 35~40° C. to 60~80° C. within 10 seconds, expanded by applying a pressure of 500 kPa or smaller to the balloon, and cooled from the temperature attained by the heating to a temperature of 45° C. or lower within 10 seconds; and

(10) Use of the medical apparatus according to any one of (3), (4), (5) and (6) for treating a portion of disease of the living organ.

Figure 1:
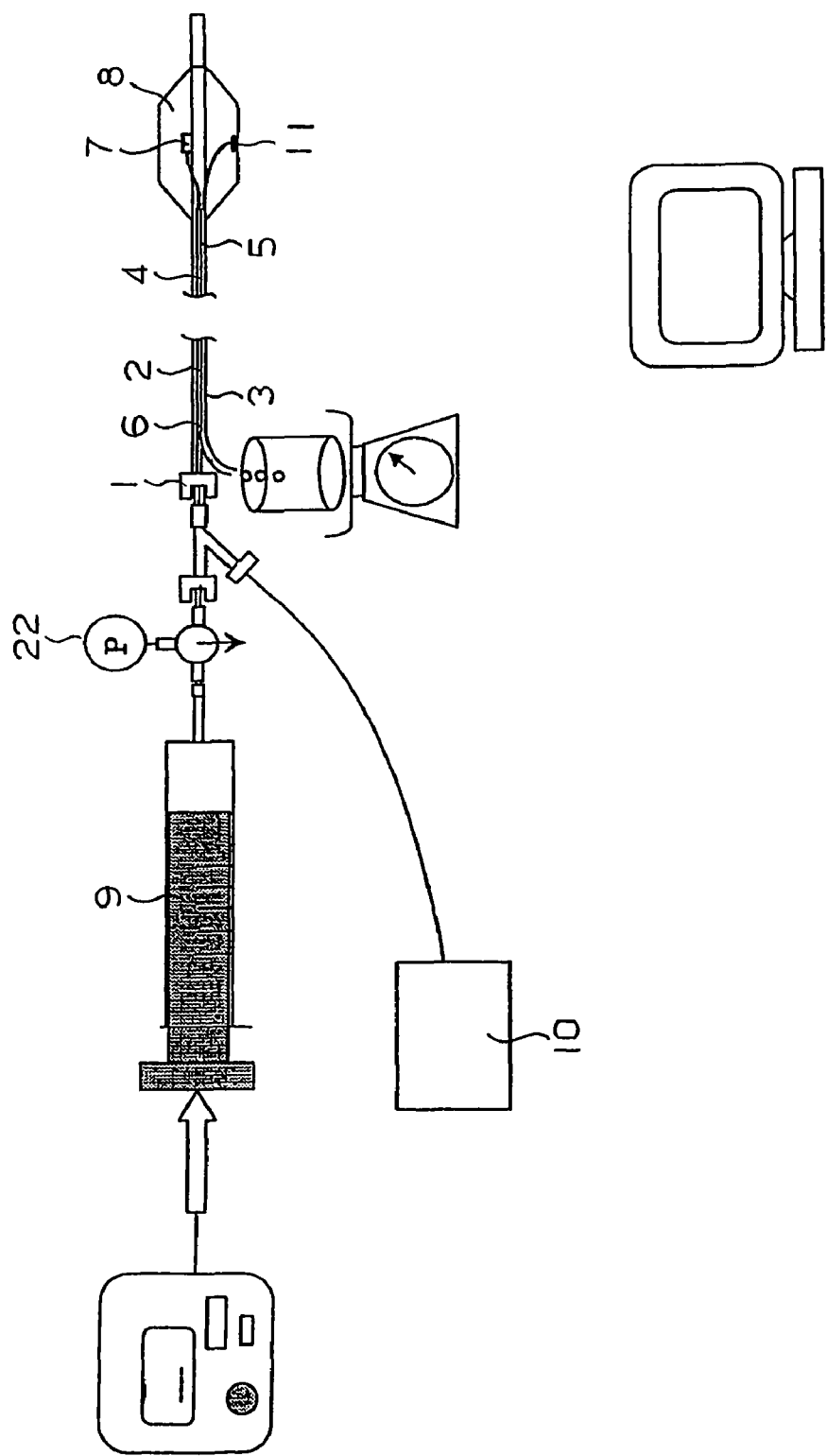
FIG. 1 shows a diagram exhibiting an embodiment of the balloon catheter of the present invention.

The numbers and characters in the figures have the meanings as listed in the following:

The numbers and characters in the figures have the meanings as listed in the following:
1: A proximally disposed connecting member
2: A lumen for introducing a fluid
3: A lumen for discharging a fluid
4: An optical fiber
5: A lead wire to a temperature sensor
6: A catheter shaft
7: A heat-generating member
8: A balloon
9: An apparatus for introducing a fluid
10: An apparatus emitting laser beams
11: A temperature sensor
12: A proximally disposed connecting member
13: A lumen for introducing a fluid
14: A lumen for discharging a fluid
15: An optical fiber
16: A lead wire to a temperature sensor
17: A catheter shaft
18: A heat-generating member
19: A balloon
20: A temperature sensor
21: A tip portion of an optical fiber
22: Means for detecting pressure

DESCRIPTION OF THE PREFERRED EMBODIMENTS

The balloon catheter of the present invention comprises a proximally disposed connecting member comprising an inlet for a fluid, an outlet for a fluid and an inlet for energy, a balloon, a catheter shaft comprising a lumen for introducing the fluid into the balloon and a lumen for discharging the fluid from the balloon and a heat-generating member. The proximally disposed connecting member and a proximal portion of the catheter shaft are connected to each other, a distal portion of the catheter shaft and a proximal portion of the balloon is connected to each other, and the heat-generating member is in contact with the fluid at the inside of the balloon or in a distal portion of the catheter shaft. ("Proximal" or "proximally disposed" means that a position or a portion is located close to the portion for manipulating. "Distal" means that a position or a portion is located far from the portion for manipulating.)

FIG. 1 shows a diagram exhibiting an embodiment of the balloon catheter of the present invention. The balloon catheter of the present embodiment comprises a proximally disposed connecting member 1 comprising an inlet for a fluid, an outlet for a fluid and an inlet for energy, a balloon 8, a catheter shaft 6 through which a lumen 2 for introducing the fluid into the balloon and a lumen 3 for discharging the fluid from the balloon, an optical fiber 4 for introducing laser beams and a lead wire to a temperature sensor 5 are inserted, and a heat-generating member 7. An apparatus for introducing a fluid 9 and a apparatus emitting laser beams 10 are disposed at proximal positions. A temperature sensor 11 is disposed at the inside of the balloon.

This catheter is inserted into a living organ so that the balloon reaches the portion of a disease. The balloon is expanded by introducing a fluid into the balloon. Laser beams are emitted, and the energy of the laser beams is converted into heat by the heat-generating member. The temperature of the surface of the balloon is raised to a prescribed temperature by the obtained heat in a short time. After a tubular organ is kept being expanded while the pressure and the temperature are kept at prescribed values for a prescribed time, the emission of the laser beams is stopped, and the surface of the balloon is cooled in a short time with a fluid at the room temperature. In this manner, the tubular organ can be expanded without causing damage to the living organ.

Figure 2:
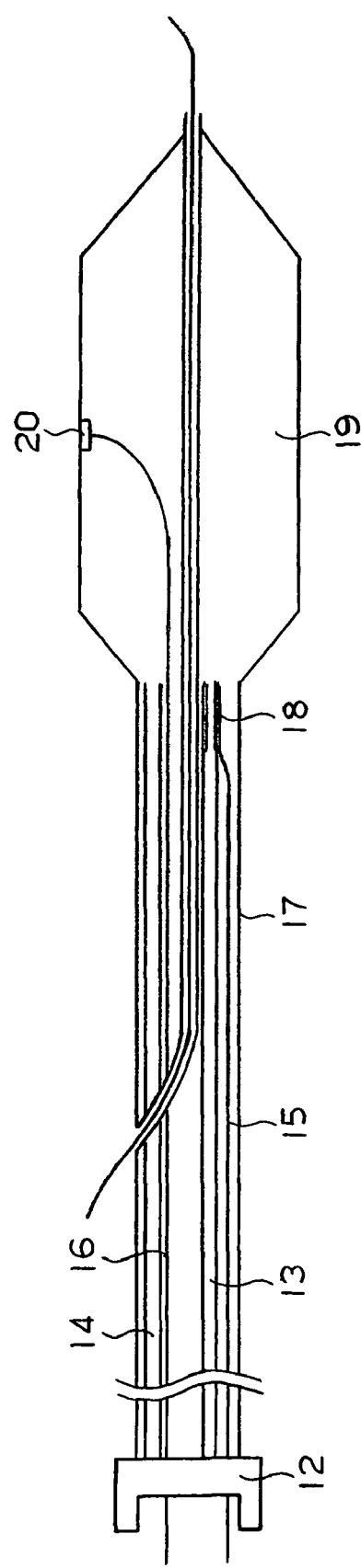
FIG. 2 shows a diagram exhibiting another embodiment of the balloon catheter of the present invention.

FIG. 2 shows a diagram exhibiting another embodiment of the balloon catheter of the present invention. The balloon catheter of the present embodiment comprises a proximally disposed connecting member 12 comprising an inlet for a fluid, an outlet for a fluid and an inlet for energy, a balloon 19, a catheter shaft 17 through which a lumen 13 for introducing the fluid into the balloon and a lumen 14 for discharging the fluid from the balloon, an optical fiber 15 for introducing laser beams and a lead wire to a temperature sensor 16 are inserted, and a heat-generating member 18. A temperature sensor 20 is disposed at the inside of the balloon.

The shapes of the lumen for introducing the fluid into the balloon and the lumen for discharging the fluid from the balloon are not particularly limited. Two tubes may be used separately as the two lumens. As another shape, the inside of a single tube having a circular sectional shape may be separated into two portions with an inner wall extending in the longitudinal direction, and the formed two portions may be used as the two lumens. In combination with the lumens for the fluid, for example, a lead wire for passing a high frequency electric current as the energy and a lumen for inserting a thermocouple for the measurement of the temperature may be inserted.

As shown in the embodiments shown in FIGS. 1 and 2, in the balloon catheter of the present invention, the proximally disposed connecting member and a proximal portion of the catheter shaft are connected to each other, and a distal portion of the catheter shaft and a proximal portion of the balloon is connected to each other. In the embodiment shown in FIG. 1, the heat-generating member 7 is in contact with the fluid at the inside of the balloon 8. In the embodiment shown in FIG. 2, the heat-generating member 18 is in contact with the fluid introduced into the balloon 19 at a position in a distal portion of the catheter shaft 17. In the embodiment shown in FIG. 2, the method for bringing the heat-generating member into contact with the fluid introduced into the balloon is not particularly limited. For example, the heat-generating member may be disposed at the inside of the lumen for introducing a fluid into the balloon in a distal portion of the catheter shaft, or a portion of the lumen for introducing a fluid into the balloon at a distal portion of the catheter shaft may be formed into the heat-generating member. The heat-generating member may also be disposed at the outside of the discharging end of the lumen for introducing a fluid into the balloon in a distal portion of the catheter shaft.

In the embodiment shown in FIG. 1, the heat-generating member 7 as the device for converting the energy of laser beams is disposed at the inside of the balloon. In the embodiment shown in FIG. 2, the polymer at a portion at the discharging end of the lumen for introducing a fluid into the balloon is removed, and the exposed metal braid works as the heat-generating member 18 of the device for converting the energy of laser beams. When the heat-generating member is disposed at a proximal position of the catheter shaft, the heat energy of the heated fluid is lost to blood, body fluids and tissues by conduction, and this causes not only a decrease in the efficiency of heating but also unstable control of the temperature of the balloon. Since the heat-generating member is present at the inside of the balloon or in a distal portion of the catheter shaft in the balloon catheter of the present invention, the fluid is heated at the inside of the balloon or immediately before being introduced into the balloon, and the temperature of the balloon can be accurately controlled with stability.

The form of the balloon catheter of the present invention is not particularly limited. The form may be a form of the monorail type having a guide wire lumen between the distal portion of the balloon and a guide wire port open at an intermediate portion of the catheter shaft, or a form of the over-the-wire type having a guide wire lumen inserted through the entire length of the catheter.

In the balloon catheter of the present invention, the energy supplied to the heat-generating member is not particularly limited. Examples of the energy include high frequency electric current of about 500 Hz and laser beams. When the high frequency electric current is used as the energy, a heat-generating material such as a wire of a Ni—Cr alloy, a heat-generating material containing carbon and tungsten can be used as the heat-generating member. When the laser beams are used as the energy, a metal member absorbing the laser beams and converting the beams into heat such as stainless steel, chromium steel, ferrite steel and a nickel/titanium ultraelastic alloy can be used as the heat-generating member. By forming the metal member into a shape of a blade, a coil, a net, a braid or wool, hardening of the catheter shaft can be prevented, and excellent operability can be maintained. The metal member can also be used as the X-ray marker.

In the balloon catheter of the present invention, when the heat-generating member is disposed at the inside of the balloon, it is preferable that a thermosetting resin having a great heat resistance is used as the material of the balloon. By using a thermosetting resin as the material of the balloon, damage caused by the contact of the heat-generating member and the balloon with each other can be prevented. In the balloon catheter of the present invention, when the heat-generating member is disposed in a distal portion of the catheter shaft, a thermoplastic resin can be used as the material of the balloon since there is no possibility that the heat-generating member and the balloon are in contact with each other. The thermoplastic resin can be formed into a thin film with more excellent productivity than the thermosetting resin, and the balloon can be produced economically in accordance with the blow molding or the like process. Since a thin film of the thermoplastic resin has a small modulus, the properties for folding, re-wrapping and insertion into a body cavity are excellent, and the folded balloon deforms delicately to follow the curved shape of the body cavity and can be inserted with a small resistance.

In the balloon catheter of the present invention, heat is transferred to the fluid through the contact of the heat-generating member with the fluid at the inside of the catheter or in the distal portion of the catheter shaft. In other words, since the heat transfer takes place in the field of flow, the over-all heat transfer coefficient is great, and the fluid can be heated efficiently. Since the fluid is heated to the prescribed temperature at the inside of the balloon or is introduced into the balloon immediately after being heated to the prescribed temperature, the entire portions at the surface and at the inside of the balloon can be kept at the same temperature.

In the balloon catheter of the present invention, when the heat-generating member is in contact with the fluid in the distal portion of the catheter shaft, it is preferable that the balloon comprises a thermoplastic resin and is produced in accordance with the blow molding process. In the present invention, not only thermoplastic resins having no crosslinking at all but also thermoplastic resins having partial crosslinking can be used as the thermoplastic resin as long as the thermoplastic resin can be molded in accordance with the extrusion molding process or the blow molding process. Examples of the thermoplastic resin used in the present invention include polyolefin resins, polyamide resin, polyamide elastomers, polyether amide resins, polyester resins, polyester elastomers, fluororesins, polyurethane resins, silicone resins, natural rubber and synthetic rubbers.

The process for producing the balloon comprising the thermoplastic resin in accordance with the blow molding is not particularly limited. For example, the balloon can be obtained by cutting a tube obtained from the thermoplastic resin in accordance with the extrusion molding process to form a parison, followed by blow molding the obtained parison with biaxial stretching. The stretching ratio in the blow molding with biaxial stretching is not particularly limited. It is preferable that the stretching ratio is in the range of 1.5 to 5 in the longitudinal direction and in the range of 2 to 5 in the radial direction, and more preferably in the range of 2 to 4 in the longitudinal direction and in the range of 2.5 to 4 in the radial direction.

In the present invention, it is preferable that the temperature of the blow molding to prepare the balloon is 100° C. or higher, more preferably 105° C. or higher and most preferable 110° C. or higher. Since a physiological saline or a contrast medium for X-ray using water as the solvent or the dispersion medium is used as the medium for heating the balloon in almost all cases, the temperature of the balloon does not exceed 100° C. in almost all cases. Therefore, when the blow molding to prepare the balloon is conducted at a temperature exceeding 100° C., the balloon can be used safely with little possibility of deformation by heating during the used of the balloon catheter. The balloon produced in accordance with the so-called cold blowing process at a temperature of about 40 to 80° C. tends to show a decrease in the diameter of the balloon due to the reversion of the shape when the balloon is heated at a temperature higher than that of the blow molding although the strength relative to the thickness is great due to the orientation of the polymer with crystallization. In the present invention, since the living organ is expanded without applying a great pressure to the balloon, a great resistance to pressure is not necessary for the balloon, and the balloon prepared in accordance with the blow molding process at a high temperature can be used with excellent stability under heating although the blow molding process at a high temperature has heretofore been considered to cause insufficient strength.

In the balloon catheter of the present invention, it is preferable that the entire catheter shaft or the distal portion of the catheter shaft where the heat-generating member is disposed comprises a heat-resistant material. Examples of the heat-resistant material include Ni—Ti ultraelastic alloys, stainless steel, polyimides, polyether imides, polysulfones, polyether ether ketones and composite materials comprising these materials. Since these materials have a suitable flexibility in combination with the heat resistance, the catheter shaft exhibiting an excellent balance can be obtained. By forming at least the distal portion of the catheter shaft, where the heat-generating member is disposed, with the heat-resistant material, the balloon catheter can be used safely without possibility of causing damages to the catheter shaft by excessive heating.

The medical apparatus of the present invention comprises a balloon catheter described above and a temperature sensor disposed at the inside of the balloon or at the catheter shaft at a distal position from the heat-generating member. The fluid at a low temperature is introduced from the inlet for a fluid, flows through the inside of the balloon and is discharged from the outlet for a fluid. Energy is introduced from the inlet for energy into the catheter shaft, is converted into heat by the heat-generating member and heats the fluid. A living organ is heated and cooled for a medical treatment by the balloon which is heated and cooled, respectively, with the fluid.

The medical apparatus of the present invention can heat the fluid efficiently and raise the temperature of the balloon in a short time since heat is transferred from the heat-generating member disposed at the inside of the balloon or in the distal portion of the catheter shaft to the fluid introduced into the balloon in the field of flow. The temperature of the balloon can be accurately controlled by sending the signal detected by the temperature sensor to the apparatus for output of the energy and controlling the amount of the introduced energy. Since the heat-generating member is disposed at the inside of the balloon or in the distal portion of the catheter shaft, the fluid at a low temperature flows through the inside of the balloon immediately after stopping the introduction of the energy, and the temperature of the balloon can be lowered in a short time.

A living organ is constituted with proteins containing collagen as the main component, and proteins are softened at higher temperatures similarly to ordinary polymers. The effect of heat to living cells is relatively mild with respect to the time. Necrosis of cells takes place when the cells are kept at a high temperature for a long time. Change in the physical properties of collagen in tissues of blood vessels is a physicochemical phenomenon and takes place instantaneously. Therefore, by heating a living tissue rapidly in a short time, very thin surface layers of the living tissue alone can be heated to kill the tissue or to provide the apoptosis factor without causing biological damage to deeper portions. By expanding the physicochemically softened blood vessel under a relatively small pressure, the tubular cavity for obtaining sufficient blood stream is secured without causing damage to the tissue due to excessive forces, and the stable opening of the tubular cavity can be achieved by the sufficient blood stream after the treatment.

It is preferable that the medical apparatus of the present invention has the ability of heating the balloon from 35~40° C. to 60~80° C. within 30 seconds and cooling from the temperature attained by the heating to a temperature of 45° C. or lower within 40 seconds. By heating the portion of disease of the living organ from 35~40° C. to 60~80° C. within 30 seconds and cooling from the temperature attained by the heating to a temperature of 45° C. or lower within 40 seconds, the medical treatment can be conducted without causing great invasion to the living organ.

It is preferable that the medical apparatus of the present invention comprises a means for detecting the pressure, and the balloon can be expanded by applying a pressure with adjustment of the degrees of opening of the inlet for a fluid and the outlet for a fluid or the pressure of the introduced fluid. By inserting the balloon into the stenosis portion of the living organ and expanding the stenosis portion by expanding the balloon while the pressure is controlled using the means for detecting a pressure to prevent application of an excessively great pressure, the medical treatment can be conducted without tearing or degrading the tissue of the blood vessel by a great force.

Figure 3:
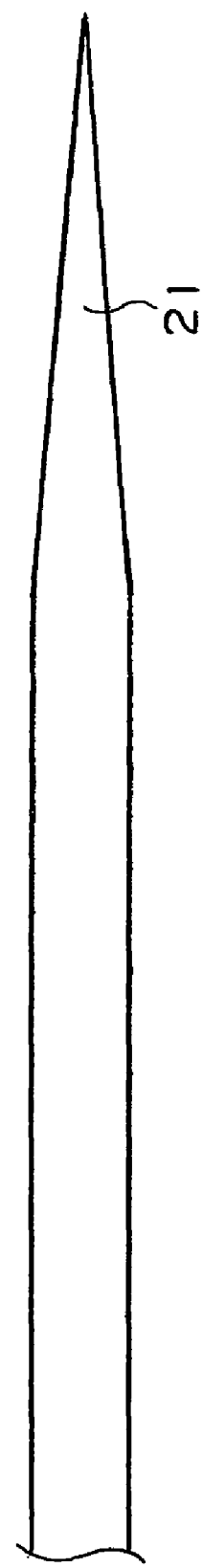
FIG. 3 shows a side view of the tip portion of an optical fiber having the cone shape.

It is preferable that the medical apparatus of the present invention uses laser beams as the energy. Laser beams show quick responses, and a great output can be obtained using a small apparatus. The tip portion of the optical fiber for introduction of the laser beams may have a cone shape or a round shape having the diameter gradually decreasing towards the tip. Alternatively, the tip portion of the optical fiber may have a rough surface. FIG. 3 shows a side view of a cone shape of the tip portion of an optical fiber having the diameter gradually decreasing towards the tip. Due to the cone shape, the round shape or the rough surface of the tip portion 21 of the optical fiber, the temperature at the inside of the balloon can be maintained uniformly. It is preferable that the tip portion of the optical fiber has, among these shapes, a cone shape having a diameter gradually decreasing towards the tip.

The medical apparatus of the present invention can be used for a method for treating diseases in which it is desirable to heat a very thin surface layer of the living tissue of the portion of disease. Using the medical apparatus of the present invention, it is possible for example, to make the very thin surface layers of the living tissue of the portion of disease alone to die by heating the tissue rapidly in a short time or to provide the apoptosis factor without causing biological damage to deeper portions. It is particularly useful for the method of treating stenosis in a living organ. By expanding the physicochemically softened blood vessel, the softening being effected by rapid heating by the apparatus of the present invention and the expanding being attained by expanding the balloon under a relatively small pressure, the tubular cavity for obtaining sufficient blood stream is secured without causing damage to the tissue due to excessive forces, and the stable opening of the tubular cavity can be achieved by the sufficient blood stream after the treatment.

In applying the medical apparatus of the present invention to a patient in need of such treatment for treating a living organ, the catheter is inserted into a living organ so that the balloon of the catheter reaches the portion of disease and the fluid at low temperature is introduced into the balloon and energy is introduced to the heat-generating member during a period of time to effect the portion of disease is heated to a temperature level which is effective for the treatment of the portion of a disease. The level of the temperature at which the portion of a disease is heated and the period of time during which the energy is introduced to the heat-generating member are not particularly limited. They are determined so that the effect of heating the portion of a disease is effective for the treatment, but not excessively resulting in damage to a living organ. After the prescribed heating, the energy is cut off and the portion of a disease is cooled quickly by the fluid at a lower temperature flowing into the balloon to the temperature level at which the living organ is not damaged. If desired, the balloon is expanded by applying a pressure to an appropriate level.

In applying the medical apparatus of the present invention for treating stenosis of a tubular organ, a portion of a disease of the living organ is heated from 35~40° C. to 60~80° C. within 30 seconds, expanded by applying a pressure of 500 kPa or smaller to the balloon and cooled from the temperature attained by the heating to a temperature of 45° C. or lower within 40 seconds. In the method of the present invention, the order of heating the portion of a disease and expanding the balloon by application of a pressure is not particularly limited. For example, the temperature may be raised after a pressure of 500 kPa or smaller is applied to the balloon. In this case, when the pressure of 500 kPa or smaller is applied to the balloon, the expansion of the living organ does not take place at temperatures around the room temperature, but takes place when the temperature reaches 60 to 80° C.

Figure 4:
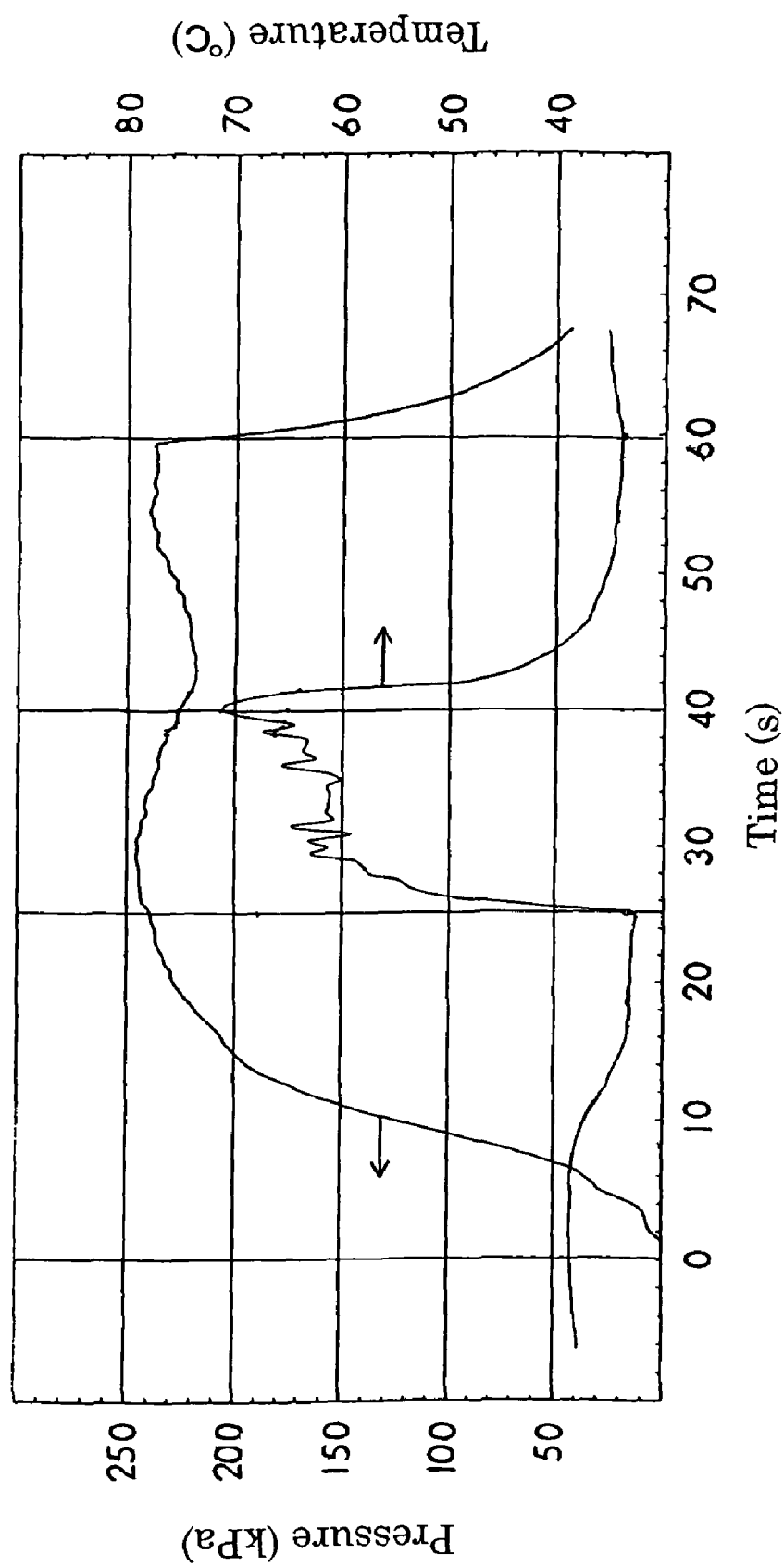
FIG. 4 shows a diagram exhibiting the change in the pressure at the inside of a balloon and the temperature at the surface of the balloon with time.

FIG. 4 shows a diagram exhibiting the changes in the pressure at the inside of the balloon and the temperature at the surface of the balloon with time. When the introduction of the fluid is started at the time of 0 second, the pressure at the inside of the balloon begins to be raised and reaches 200 kPa after 14 seconds. When the pressure at the inside of the balloon reaches 240 kPa 25 seconds after the start of the introduction of the fluid, the emission of the laser beams is started. The temperature of the balloon at the surface is rapidly raised and reaches 60° C. 4 seconds after the start of the emission of the laser beams. The emission of laser beams is controlled by switching on and off the apparatus based on the signal transferred from the temperature sensor in a manner such that the temperature at the surface of the balloon is kept in the range of 60 to 70° C. When the emission of the laser beams is stopped 15 seconds after the start of the emission of the laser beams, the balloon is rapidly cooled with the fluid, and the temperature at the surface of the balloon is lowered to 45° C. 3 seconds after the stopping of the emission of the laser beams. The introduction of the fluid is stopped 20 seconds after the stopping of the emission of the laser beams, and the pressure at the inside of the balloon is lowered.

In the method of the present invention, when the time required to raise the temperature from 35~40° C. to 60~80° C. exceeds 30 seconds, there is the possibility that the thickness of the living organ decreases due to damage and the stenosis takes place with passage of time. When the temperature at the portion of a disease of the living organ is lower than 60° C., there is the possibility that the expansion is insufficient under a pressure of the balloon of 500 kPa or smaller. When the pressure of the balloon exceeds 500 kPa, there is the possibility that the tissue of the living organ is torn or degraded. When the time of lowering the temperature to 45° C. or lower exceeds 40 seconds, there is the possibility that the thickness of the living organ decreases due to damage, and the stenosis takes place with passage of time.

The method of treating a living organ of the present invention can be advantageously applied to medical treatments of portions of a disease of a blood vessel such as the percutanuous transluminal coronary angioplasty (PTCA). It is considered that, when a cell of a smooth muscle is damaged and the tissue is restored by the stem cell, abnormal information due to the damage is transferred or abnormal division of a stem cell takes place, and the recurrence of stenosis of a tubular organ takes place. It is occasionally conducted that a blood vessel for the treatment is cut by so-called TEC or a rotablator so that the outer membrane alone is left remaining, and a stent is disposed thereafter. When a necessary tissue is removed by the cutting, the tissue of the inner skin is not stabilized even when the tissue is formed, and this is considered to cause the recurrence of the stenosis. In contrast, in accordance with the method for treating a living organ of the present Invention, the surface of the tissue of the blood vessel alone is heated instantaneously. The tissue of the tubular cavity is expanded by application of a small pressure without causing damage in deeper Portions of the tubular cavity, and the tissue of the blood vessel is treated safely and effectively without causing damage to the tissue of the blood vessel by an unnecessarily great force. Thus, the excellent effect of the medical treatment can be obtained.

To summarize the advantages obtained by the invention, by using the balloon catheter and the medical apparatus and in accordance with the method for treating a living organ of the present invention, a living organ can be heated and cooled within a very short time to cure a diseased tissue and a blood vessel can be expanded without damage, in particular, in application to the percutanuous transluminal coronary angioplasty (PTCA).

EXAMPLES

The present invention will be described more specifically with reference to examples in the following. However, the present invention is not limited to the examples.

Example 1 and Comparative Example 1

A medical apparatus shown in FIG. 1 was used. A catheter shaft was made of a polyamide and had an outer diameter of 1 mm and a whole length of 1,400 mm. A balloon was made of a polyimide and had an outer diameter of 3 mm and a length of 15 mm when the balloon was expanded. A lumen for introducing a fluid and a lumen for discharging a fluid each having an outer diameter of 200 μm, a quartz optical fiber having an outer diameter of 100 μm and a thermocouple were inserted through the catheter shaft.

A device for converting laser energy made of stainless steel and a contact point for the thermocouple were placed at the inside of the balloon. To a proximal portion of the lumen for introducing a fluid, a pressure sensor, a pressure-resistant syringe having a volume of 20 ml and an apparatus for introducing a fluid composed of an auto-injector were connected, and a fluid which was a mixture of a contrast medium and a physiological saline in a ratio of the amounts by volume of 1:1 was introduced while a prescribed pressure was maintained. The fluid flowing out of the end of the lumen for discharging a fluid was received into a vessel placed on a microbalance and weighed. To a proximal position of the quartz optical fiber, a YAG laser having an output of 5 W was connected. The information from the pressure sensor and the temperature sensor and the weight obtained by the microbalance were input into a computer, and the flow rate of the heating medium and the output of the laser were controlled so that the prescribed pressure, rate of raising the temperature, maintained temperature and rate of lowering the temperature in the balloon were achieved.

In advance, the catheter shaft and the balloon of the medical apparatus were placed in a tank kept constant at 37° C., and the condition of the operation for achieving the prescribed time, temperature and pressure was obtained. It was confirmed that the prescribed relations between the time, the temperature and the pressure were achieved when the medical apparatus was operated under the obtained condition.

A left hind leg of a rabbit was used in Example 1, and a right hind leg was used in Comparative Example 1. Into each of two inguinal arteries, a peel off sheath was inserted, and the catheter shaft was inserted through the sheath. The fluid was introduced through the catheter shaft, and the pressure was kept at 200 kPa. In Example 1 in which the left hind leg was used, the temperature at the surface of the balloon was raised from 37° C. to 70° C. in 30 seconds, kept at 70° C. for 20 seconds and lowered to 45° C. in 40 seconds. In Comparative Example 1 in which the right hind leg was used, the same procedures as those conducted in Example 1 were conducted except that the temperature was raised in 40 seconds and lowered in 50 seconds. After the bleeding was stopped, the rabbit was returned to a cage, bred there for 2 months and killed for examination. The rabbit was then dissected, and the condition of blood vessels was observed. The inner diameter of a blood vessel $d_1$ at the treated portion and the inner diameter of a blood vessel $d_0$ in an adjacent portion were measured, and the ratio of the inner diameters of blood vessels $d_1/d_0$ was obtained. Based on the result of the observation and the ratio of inner diameters of blood vessels obtained above, the overall evaluation was made.

Almost no abnormality was found in the blood vessel of the left hind leg. The ratio of the inner diameters of blood vessels was 1.3. The result of the overall evaluation was good. The thickness of the blood vessel of the right hind leg was found to have decreased. The ratio of the inner diameters of blood vessels was 0.7. The result of the overall evaluation was poor.

Example 2 and Comparative Example 2

Similarly to Example 1 and Comparative Example 1, a left hind leg of a rabbit was used in Example 2, and a right hind leg was used in Comparative Example 2. In Example 2 in which the left hind leg was used, the temperature at the surface of the balloon was raised from 37° C. to 70° C. in 20 seconds, kept at 70° C. for 10 seconds and lowered to 45° C. in 20 seconds. In Comparative Example 2 in which the right hind leg was used, the temperature at the surface of the balloon was raised from 37° C. to 90° C. in 10 seconds, kept at 90° C. for 10 seconds and lowered to 45° C. in 10 seconds.

After two months, almost no abnormality was found in the blood vessel of the left hind leg. The ratio of the inner diameters of blood vessels was 1.3. The result of the overall evaluation was good. The thickness of the blood vessel of the right hind leg was found to have decreased. The ratio of the inner diameters of blood vessels was 0.7. The result of the overall evaluation was poor.

Examples 3 and 4

Similarly to Example 1 and Comparative Example 1, a left hind leg of a rabbit was used in Example 3, and a right hind leg was used in Example 4. In Example 3 in which the left hind leg was used, the temperature at the surface of the balloon was raised from 37° C. to 80° C. in 10 seconds, kept at 80° C. for 10 seconds and lowered to 45° C. in 10 seconds. In Example 4 in which the right hind leg was used, the same procedures as those conducted in Example 3 were conducted except that the temperature at the surface of the balloon was raised to 70° C. and kept at 70° C. for 10 seconds.

After two months, almost no abnormality was found in the blood vessel of the left hind leg. The ratio of the inner diameters of blood vessels was 1.5. The result of the overall evaluation was good. No abnormality was found at all in the blood vessel of the right hind leg. The ratio of the inner diameters of blood vessels was 1.5. The result of the overall evaluation was excellent.

Examples 5 and 6

Similarly to Example 1 and Comparative Example 1, a left hind leg of a rabbit was used in Example 5, and a right hind leg was used in Example 6. In Example 5 in which the left hind leg was used, the temperature at the surface of the balloon was raised from 37° C. to 65° C. in 10 seconds, kept at 65° C. for 10 seconds and lowered to 45° C. in 10 seconds. In Example 6 in which the right hind leg was used, the same procedures as those conducted in Example 5 were conducted except that the temperature at the surface of the balloon was raised to 60° C. and kept at 60° C. for 10 seconds.

After two months, no abnormality was found at all in the blood vessel of the left hind leg. The ratio of the inner diameters of blood vessels was 1.4. The result of the overall evaluation was excellent. No abnormality was found at all in the blood vessel of the right hind leg, either. The ratio of the inner diameters of blood vessels was 1.4. The result of the overall evaluation was excellent.

Examples 7 and 8

Similarly to Example 1 and Comparative Example 1, a left hind leg of a rabbit was used in Example 7, and a right hind leg was used in Example 8. In Example 7 in which the left hind leg was used, the temperature at the surface of the balloon was raised from 37° C. to 57° C. in 10 seconds, kept at 57° C. for 10 seconds and lowered to 45° C. in 10 seconds. In Example 8 in which the right hind leg was used, the same procedures as those conducted in Example 7 were conducted except that the temperature at the surface of the balloon was raised to 55° C. and kept at 55° C. for 10 seconds.

After two months, no abnormality was found at all in the blood vessel of the left hind leg. The ratio of the inner diameters of blood vessels was 1.2. The result of the overall evaluation was good. No abnormality was found at all in the blood vessel of the right hind leg, either. The ratio of the inner diameters of blood vessels was 1.1. The result of the overall evaluation was good.

Example 9 and Comparative Example 3

A left hind leg of a rabbit was used in Example 9, and a right hind leg was used in Comparative Example 3. Into each of two inguinal arteries, the catheter shaft was inserted, and the heating medium was introduced through the catheter shaft. The pressure in the left hind leg was kept at 400 kPa, and the pressure in the right hind leg was kept at 600 kPa. In both hind legs, the temperature at the surface of the balloon was raised from 37° C. to 70° C. in 10 seconds, kept at 70° C. for 10 seconds and lowered to 45° C. in 10 seconds.

After two months, no abnormality was found at all in the blood vessel of the left hind leg. The ratio of the inner diameters of blood vessels was 1.5. The result of the overall evaluation was excellent. The thickness of the media in the blood vessel of the right hind leg was found to have increased although the diameter of the blood vessel increased. The ratio of the inner diameters of blood vessels was 1.2. The result of the overall evaluation was fair to poor.

Comparative Example 4 and Comparative Example 5

A left hind leg of a rabbit was used in Comparative Example 4, and a right hind leg was used in Comparative Example 5. Into each of two inguinal arteries, the catheter shaft was inserted, and the heating medium at the room temperature was introduced through the catheter shaft without irradiation with the laser beams. After the pressure in the left hind leg was kept at 1,200 kPa for 10 seconds, and the pressure in the right hind leg was kept at 400 kPa for 10 seconds, the introduction of the heating medium was stopped.

After two months, it was found that the blood vessel in the left hind leg was damaged and the thickness increased. The ratio of the inner diameters of blood vessels was 0.8. The result of the overall evaluation was poor. Almost no abnormality was found in the blood vessel of the right hind leg. However, the blood vessel was not expanded. The ratio of the inner diameters of blood vessels was 1.0. The result of the overall evaluation was poor.

TABLE 1

| | Pressure (kPa) | Time of raising temperature (second) | Temperature of balloon (° C.) | Time of keeping temperature (second) |
|---|---|---|---|---|
| Comparative Example 1 | 200 | 40 | 70 | 20 |
| Example 1 | 200 | 30 | 70 | 20 |
| Example 2 | 200 | 20 | 70 | 10 |
| Comparative Example 2 | 200 | 10 | 90 | 10 |
| Example 3 | 200 | 10 | 80 | 10 |
| Example 4 | 200 | 10 | 70 | 10 |
| Example 5 | 200 | 10 | 65 | 10 |
| Example 6 | 200 | 10 | 60 | 10 |
| Example 7 | 200 | 10 | 57 | 10 |
| Example 8 | 200 | 10 | 55 | 10 |
| Example 9 | 400 | 10 | 70 | 10 |
| Comparative Example 3 | 600 | 10 | 70 | 10 |
| Comparative Example 4 | 1200 | — | 37 | 10 |
| Comparative Example 5 | 400 | — | 37 | 10 |

| | Time of lowering temperature (second) | Condition of blood vessel | Ratio of inner diameters of blood vessels ($d_1/d_0$) | Overall evaluation |
|---|---|---|---|---|
| Comparative Example 1 | 50 | thickness decreased | 0.7 | poor |
| Example 1 | 40 | almost no abnormality | 1.3 | good |
| Example 2 | 20 | almost no abnormality | 1.3 | good |
| Comparative Example 2 | 10 | thickness decreased | 0.9 | poor |
| Example 3 | 10 | almost no abnormality | 1.5 | good |
| Example 4 | 10 | no abnormality at all | 1.5 | excellent |
| Example 5 | 10 | no abnormality at all | 1.4 | excellent |
| Example 6 | 10 | no abnormality at all | 1.4 | excellent |
| Example 7 | 10 | no abnormality at all | 1.2 | good |
| Example 8 | 10 | no abnormality at all | 1.1 | good |
| Example 9 | 10 | no abnormality at all | 1.5 | excellent |
| Comparative Example 3 | 10 | thickness increased | 1.2 | fair to poor |
| Comparative Example 4 | — | damaged thickness increased | 0.8 | poor |
| Comparative Example 5 | — | almost no abnormality | 1.0 | poor |

When the results of Example 1 and Comparative Example 1 are compared, the excellent result was obtained in Example 1 in which the temperature was raised in 30 seconds and lowered in 40 seconds. In contrast, the thickness of the blood vessel decreased, and the blood vessel was not expanded in Comparative Example 1 in which the times for raising and lowering the temperature were each longer than the above by 10 seconds even though the pressure applied to the balloon and the temperature at the surface of the balloon were kept at the same as those in Example 1, i.e., 200 kPa and 70° C., respectively. These results show that it is important for obtaining the excellent results that the surface of the balloon is heated and cooled in a short time.

When the results of Example 3 and Comparative Example 2 are compared, the excellent result was obtained in Example 3 in which the temperature of the surface of the balloon was 80° C. In contrast, the thickness of the blood vessel decreased, and the blood vessel was not expanded in Comparative Example 2 in which the temperature of the surface of the balloon was 90° C. even though the pressure applied to the balloon and the times for raising and lowering the temperature were kept at the same as those in Example 3, i.e., 200 kPa and 10 seconds, respectively. These results show that it is important for obtaining the excellent results that the temperature of the surface of the balloon is not excessively high.

In Examples 4 to 6 in which the pressure applied to the balloon was 200 kPa, the temperature of the surface of the balloon was 60~70° C. and the temperature was raised and lowered each in 10 seconds, the excellent results were obtained in that no abnormality was found at all in the condition of the blood vessel, and the degree of expansion of the blood vessel was great.

When the results of Example 9 and Comparative Example 3 are compared, the excellent result was obtained in Example 9 in which the pressure applied to the balloon was 400 kPa. In contrast, the thickness of the media in the blood vessel increased and, as the result, the ratio of the inner diameters of the blood vessels increased only to 1.2 in Comparative Example 3 in which the pressure applied to the balloon was increased to 600 kPa even though the temperature of the surface of the balloon and the times for raising and lowering the temperature were kept at the same as those in Example 9, i.e., 70° C. and 10 seconds, respectively. These results show that an excessively great pressure applied to the balloon gives the inferior result of the evaluation.

Example 10

A medical apparatus shown in FIG. 2 was used. A balloon was made of a polyamide [manufactured by UBE KOSAN Co., Ltd.; UBE NYLON 5033J12; the hardness: R80], had a diameter of 3 mm, a length of 15 mm and a thickness of 20 μm and was prepared in accordance with the blow molding process at a blowing temperature of 100° C. under a blowing pressure of 700 kPa. A catheter shaft was a tube having a braid of stainless steel, made of a polyamide tube and having an outer diameter of 1 mm, a thickness of 50 μm and a whole length of 1,400 mm. A lumen for introducing a fluid, which was a mixture of a contrast medium and a physiological saline, and a lumen for discharging the fluid each having an outer diameter of 0.45 mm and a thickness of 30 μm, a quartz optical fiber having an outer diameter of 100 μm and a thermocouple were inserted through the catheter shaft. A coating polymer by the length of 20 mm in the distal end portion of the lumen for introducing the fluid was removed so that the metal braid was exposed, and the exposed braid was used as the device for converting the laser energy. The tip of the quartz optical fiber was disposed at a position of a proximal end of the device for converting the laser energy. The temperature sensor was disposed at the central portion of the balloon.

Into an artery in the left femoral region of a rabbit, a 6F sheath was inserted, and the balloon catheter was inserted through the sheath. The mixture of a contrast medium and a physiological saline in a ratio of the amounts by volume of 1:1 was continuously introduced under a pressure using a pump for injecting a contrast medium, and the pressure applied to the balloon was kept at 200 kPa. Laser beams were emitted from a YAG laser having an output capacity of 5 W, and the temperature of the balloon was raised from 37° C. to 70° C. in 20 seconds, kept at 70° C. for 10 seconds and lowered from 70° C. to 45° C. in 20 seconds. The signal output from the temperature sensor is fed back, and the temperature was adjusted by switching on and off the laser.

The balloon exhibited an excellent property for folding and re-wrapping. The property for inserting the balloon catheter was also excellent. Only slight deformation was found in the balloon after the use. Very slight deformation was found in the catheter shaft after the use.

After the operation, the bleeding was stopped, and the rabbit was killed and dissected. The diameter of the blood vessel $d_1$ at the treated portion and the diameter of a blood vessel $d_0$ at an adjacent portion were measured, and the ratio of the two diameters $d_1/d_0$ was obtained. The condition inside the blood vessels was observed. $d_1/d_0$ was found to be 2.0. No abnormality was found in the blood vessel.

Example 11

An artery in the left femoral region of a rabbit was used for the examination under the same conditions in accordance with the same procedures as those in Example 10 except that a polyamide elastomer [manufactured by ATOFINA JAPAN Co., Ltd.; PEBAX 633SN01; the hardness: D63] was used as the material of the balloon, and a tube made of a polyamide [manufactured by UBE KOSAN Co., Ltd.; UBE NYLON 5033J12; the hardness: R80]/a polyimide [manufactured by TORAY Co., Ltd.; TI POLYMER; the hardness: E86] and having a braid of a metal was used for the catheter shaft.

The balloon exhibited an excellent property for folding and re-wrapping. The property for inserting the balloon catheter was also excellent. Only slight deformation was found in the balloon after the use. Very slight deformation was found in the catheter shaft after the use. $d_1/d_0$ was 2.0. No abnormality was found in the blood vessel.

Example 12

An artery in the left femoral region of a rabbit was used for the examination under the same conditions in accordance with the same procedures as those in Example 10 except that a tube made of a polyamide [manufactured by UBE KOSAN Co., Ltd.; UBE NYLON 5033J12; the hardness: R80] and having a braid of stainless steel and a Ti—Ni lining at the inner face was used for the catheter shaft.

The balloon exhibited an excellent property for folding and re-wrapping. The property for inserting the balloon catheter was also excellent. Slight deformation was found in the balloon after the use. No deformation was found at all in the catheter shaft after the use. $d_1/d_0$ was 2.0. No abnormality was found in the blood vessel.

Example 13

An artery in the left femoral region of a rabbit was used for the examination under the same conditions in accordance with the same procedures as those in Example 1 except that a balloon made of a polyamide [manufactured by UBE KOSAN Co., Ltd.; UBE NYLON 5033J12; the hardness: R80] and prepared in accordance with the blow molding process at a blowing temperature of 120° C. under a blowing pressure of 400 kPa was used, and a tube made of a polyamide [manufactured by UBE KOSAN Co., Ltd.; UBE NYLON 5033J12; the hardness: R80]/a polyimide [manufactured by TORAY Co., Ltd.; TI POLYMER; the hardness: E86] and having a braid of stainless steel was used for the catheter shaft.

The balloon exhibited an excellent property for folding and re-wrapping. The property for inserting the balloon catheter was also excellent. Very slight deformation was found in the balloon and the catheter after the use. $d_1/d_0$ was 2.0. No abnormality was found in the blood vessel.

Example 14

When Example 4 was conducted, an artery in the right femoral region of the rabbit was used for the examination under the same conditions in accordance with the same procedures as those in Example 4 except that a balloon made of a polyester elastomer [manufactured by TOYO BOSEKI Co., Ltd.; PELPRENE S6001; the hardness: D72] and prepared in accordance with the blow molding process at a blowing temperature of 130° C. under a blowing pressure of 600 kPa was used, and a tube made of a polyamide [manufactured by TOYO BOSEKI Co., Ltd.; PELPRENE S6001; the hardness: D72]/a polyimide [manufactured by TORAY Co., Ltd.; TI POLYMER; the hardness: E86] and having a braid of a metal was used for the catheter shaft.

The balloon exhibited an excellent property for folding and re-wrapping. The property for inserting the balloon catheter was slightly inferior. Very slight deformation was found in the balloon after the use. Very slight deformation was found in the catheter shaft after the use. $d_1/d_0$ was 2.0. No abnormality was found in the blood vessel.

Example 15

An artery in the left femoral region of a rabbit was used for the examination under the same conditions in accordance with the same procedures as those in Example 10 except that a balloon made of a polyimide [manufactured by TORAY Co., Ltd.; TI POLYMER; the hardness: E86] and prepared in accordance with the dipping process was used, and a tube made of a polyimide [manufactured by TORAY Co., Ltd.; TI POLYMER; the hardness: E86] and having a braid of stainless steel was used for the catheter shaft.

No deformation was found at all in the balloon or the catheter shaft after the use. $d_1/d_0$ was 2.0. No abnormality was found in the blood vessel.

Example 16

When Example 15 was conducted, an artery in the right femoral region of the rabbit was used for the examination under the same conditions in accordance with the same procedures as those in Example 15 except that a balloon made of a perfluoroalkoxy resin [manufactured by MITSUI-DU PONT FLUORO-CHEMICAL Co., Ltd.; TEFLON PFA; the hardness: D60] and prepared in accordance with the blow molding process at a blowing temperature of 220° C. under a blowing pressure of 700 kPa was used, and a tube made of a perfluoroalkoxy resin [manufactured by MITSUI-DU PONT FLUORO-CHEMICAL Co., Ltd.; TEFLON PFA; the hardness: D60] and having a braid of stainless steel was used for the catheter shaft.

Very slight deformation was found in the balloon after the use. No deformation was found at all in the catheter shaft after the use. $d_1/d_0$ was 2.0. No abnormality was found in the blood vessel.

Example 17

An artery in the left femoral region of a rabbit was used for the examination under the same conditions in accordance with the same procedures as those in Example 10 except that a balloon made of a polyamide [manufactured by UBE KOSAN Co., Ltd.; UBE NYLON 5033J12; the hardness: R80] and prepared in accordance with the blow molding process at a blowing temperature of 120° C. under a blowing pressure of 400 kPa was used, a tube made of a polyamide [manufactured by UBE KOSAN Co., Ltd.; UBE NYLON 5033J12; the hardness: R80]/a polyimide [manufactured by TORAY Co., Ltd.; TI POLYMER; the hardness: E86] and having a braid of stainless steel was used for the catheter shaft, and the temperature of the balloon was raised from 37° C. to 70° C. in 10 seconds, kept at 70° C. for 10 seconds and lowered from 70° C. to 45° C. in 10 seconds.

The balloon exhibited an excellent property for folding and re-wrapping. The property for inserting the balloon catheter was also excellent. Very slight deformation was found in the balloon and the catheter after the use. $d_1/d_0$ was 1.9. No abnormality was found in the blood vessel.

Comparative Example 6

When Example 17 was conducted, an artery in the right femoral region of the rabbit was used for the examination under the same conditions in accordance with the same procedures as those in Example 17 except that a balloon made of a polyamide [manufactured by UBE KOSAN Co., Ltd.; UBE NYLON 5033J12; the hardness: R80] and prepared in accordance with the blow molding process at a blowing temperature of 120° C. under a blowing pressure of 400 kPa was used, a tube made of a polyamide [manufactured by UBE KOSAN Co., Ltd.; UBE NYLON 5033J12; the hardness R80]/a polyimide [manufactured by TORAY Co., Ltd.; TI POLYMER; the hardness: E86] and having a braid of stainless steel was used for the catheter shaft, and the temperature of the balloon was raised from 37° C. to 70° C. in 40 seconds, kept at 70° C. for 10 seconds and lowered from 70° C. to 45° C. in 50 seconds.

The balloon exhibited an excellent property for folding and re-wrapping. The property for inserting the balloon catheter was also excellent. Very slight deformation was found in the balloon and the catheter after the use. $d_1/d_0$ was 2.3. The thickness of the blood vessel was found to have decreased.

The conditions of Examples 10 to 17 and Comparative Example 6 are shown in Table 2, and the results are shown in Table 3.

TABLE 2

| | Material | | Temperature of blow molding (° C.) | Pressure of blow molding (kPa) | Time (second) | | |
|---|---|---|---|---|---|---|---|
| | balloon | catheter | | | for raising to 70° C. | for keeping at 70° C. | for lowering to 45° C. |
| Example 10 | polyamide | polyamide | 100 | 700 | 20 | 10 | 20 |
| Example 11 | polyamide elastomer | polyamide/ polyimide | 100 | 700 | 20 | 10 | 20 |
| Example 12 | polyamide | polyamide/ Ni—Ti lining | 100 | 700 | 20 | 10 | 20 |
| Example 13 | polyamide | polyamide/ polyimide | 120 | 400 | 20 | 10 | 20 |
| Example 14 | polyester elastomer | polyester elastomer/ polyimide | 130 | 600 | 20 | 10 | 20 |
| Example 15 | polyimide | polyimide | dipping | | 20 | 10 | 20 |
| Example 16 | perfluoroalkoxy resin | perfluoroalkoxy resin | 220 | 700 | 20 | 10 | 20 |
| Example 17 | polyamide | polyamide/ polyimide | 120 | 400 | 10 | 10 | 10 |

TABLE 2-continued

|  | Material | | Temperature of blow molding (°C.) | Pressure of blow molding (kPa) | Time (second) | | |
|---|---|---|---|---|---|---|---|
|  | balloon | catheter |  |  | for raising to 70° C. | for keeping at 70° C. | for lowering to 45° C. |
| Comparative Example 6 | polyamide | polyamide/ polyimide | 120 | 400 | 40 | 10 | 50 |

TABLE 3

| | Deformation after use | | Condition of | Ratio of inner diameters of blood vessels |
|---|---|---|---|---|
| | balloon | catheter | blood vessel | $(d_1/d_0)$ |
| Example 10 | slight | very slight | no abnormality | 2.0 |
| Example 11 | slight | very slight | no abnormality | 2.0 |
| Example 12 | slight | none at all | no abnormality | 2.0 |
| Example 13 | very slight | very slight | no abnormality | 2.0 |
| Example 14 | very slight | very slight | no abnormality | 2.0 |
| Example 15 | none at all | none at all | no abnormality | 2.0 |
| Example 16 | slight | none at all | no abnormality | 2.0 |
| Example 17 | very slight | very slight | no change | 1.9 |
| Comparative Example 6 | very slight | very slight | thickness decreased | 2.3 |

As shown in Table 2, in Examples 10 to 14 and 17 in which the device for converting the laser energy was placed in the distal portion of the catheter shaft, the balloon made of a thermoplastic resin was used and the temperature was raised to 70° C. in 10 to 20 seconds and lowered to 45° C. in 10 to 20 seconds, the operability of the balloon catheter was excellent, the deformation of the balloon and the catheter shaft after the use was slight, and almost no abnormality was found in the blood vessel. The balloon catheter of Examples 15 and 16 in which the device for converting the laser energy was placed in the distal position of the catheter shaft and the balloon made of the polyimide resin or the fluororesin was used, showed almost no deformation of the balloon and the catheter after the use and almost no abnormality was found in the blood vessel although the operability was inferior to that in other Examples.

In contrast, in Comparative Example 6 in which the times for raising and lowering the temperature were long although the device for converting the laser energy was placed in the distal portion of the catheter shaft and the balloon made of a thermoplastic resin was used, the thickness of the blood vessel decreased.

What is claimed is:

1. A balloon catheter which comprises: (i) a proximally-disposed connecting member comprising a fluid inlet for introducing a fluid, said fluid inlet having a lumen, a fluid outlet for discharging the fluid, and an energy inlet for introducing energy; (ii) an apparatus for introducing the fluid into the fluid inlet; (iii) a balloon; (iv) a catheter shaft comprising a lumen for introducing the fluid into the balloon and a lumen for discharging the fluid from the balloon; (v) a heat-generating member; (vi) a temperature sensor; and (vii) a means for detecting pressure, wherein the proximally-disposed connecting member and a proximal portion of the catheter shaft are connected to each other, and wherein a distal portion of the catheter shaft and a proximal portion of the balloon are connected to each other, wherein the heat-generating member is in contact with the fluid in a distal portion of the catheter shaft, wherein the energy is a laser beam which is introduced into the catheter shaft from the energy inlet via an optical fiber, wherein the heat-generating member is operable to absorb the laser beam and convert the energy of the laser beam into heat, whereby the fluid is heated immediately before being introduced into the balloon, wherein the temperature sensor is disposed inside the balloon or at the catheter shaft at a distal position from the position of the heat-generating member, for control of the heat generating member while the fluid is flowing, wherein the means for detecting pressure is operable to control pressure in the balloon, as the balloon is expanded, by applying pressure with an adjustment of degrees of opening of the fluid inlet and the fluid outlet or the pressure of the fluid that is introduced, whereby a stenosis portion of a living organ into which the balloon is inserted is expanded, while the pressure in the balloon is controlled, wherein the fluid at a low temperature is introduced into the fluid inlet, and the fluid flows through the heat-generating member and thereafter the fluid flows through an inside of the balloon and is discharged from the fluid outlet, and wherein the fluid flows into the balloon from a time when introducing the fluid at the low temperature begins to a time when the laser beam is switched-off.

2. A balloon catheter according to claim 1, wherein the balloon is made from a thermoplastic resin and is prepared by blow molding a parison obtained from the extrusion of the thermoplastic resin at a temperature of 100° C. or higher and at a biaxial stretching ratio of 1.5 to 5 in the longitudinal direction and 2 to 5 in the radial direction.

3. A balloon catheter according to claim 2, wherein the thermoplastic resin is a resin selected from the group consisting of a polyolefin resin, a polyamide resin, a polyamide elastomer, a polyether amide resin, a polyester resin, a polyester elastomer, a fluororesin, a polyurethane resin, a silicone resin, a natural rubber and a synthetic rubber.

4. A balloon catheter according to claim 3, wherein the thermoplastic resin is a polyamide resin.

5. A balloon catheter according to claim 4, wherein the catheter shaft is made of a material selected from the group consisting of Ni—Ti ultra-elastic alloy, a stainless steel, a polyimide, a polyether imide, a polysulfone, a polyether ether ketone and a composite material comprising these materials.

6. A balloon catheter according to claim 2, wherein the catheter shaft is made of a material selected from the group consisting of a Ni—Ti ultra-elastic alloy, a stainless steel, a polyimide, a polyether imide, a polysulfone, a polyether ether ketone and a composite material comprising these materials.

7. A method for treating a patient which comprises the steps of:
  inserting the balloon catheter according to claim 1 into a living organ of a patient to be treated,
  introducing the fluid at a low temperature into the fluid inlet, and the fluid flows through a heating apparatus and thereafter flows through the inside of the balloon and is discharged from the fluid outlet, and wherein the fluid flows into the balloon from a time when introducing the fluid at the low temperature begins to a time when the laser beam is switched-off,
  sensing the temperature of the fluid which is flowing with a temperature sensor disposed in the fluid,
  controlling a heating of the fluid, based on a temperature sensed, before the fluid is introduced into the balloon,
  introducing the laser beam to the heat-generating member to heat the fluid, which then heats the living organ,
  detecting the pressure in the balloon to control the pressure in the balloon as the balloon is expanded by applying pressure with an adjustment of degrees of opening of the fluid inlet and the fluid outlet, or the pressure of the introduced fluid, whereby a stenosis portion of the living organ is expanded, while the pressure in the balloon is controlled, and
  controlling the cooling of the living organ by switching-off the laser beam.

8. A medical apparatus which comprises the balloon catheter according to claim 1, which is operable to control the temperature of the fluid which is flowing to heat the balloon from a range of 35 to 40° C. to a range of 60 to 80° C. within 30 seconds and cool the balloon from the temperature attained by the heating to a temperature of 45° C. or lower within 40 seconds.

9. A medical apparatus according to claim 8, wherein the balloon is made from a thermoplastic resin and is prepared by blow molding a parison obtained from the extrusion of the thermoplastic resin at a temperature of 100° C. or higher and at a biaxial stretching ratio of 1.5 to 5 in the longitudinal direction and 2 to 5 in the radial direction, and the heat-generating member is in contact with the fluid in the distal portion of the catheter shaft.

10. A method for treating a patient comprising the steps of:
  providing a medical apparatus which comprises the balloon catheter according to claim 1,
  inserting the balloon catheter of said apparatus into a living organ of a patient to be treated, so that the balloon of said catheter reaches a portion of a diseased tissue of the living organ,
  introducing the fluid at a low temperature from the fluid inlet, and the fluid flows through the inside of the balloon and is discharged from the fluid outlet, wherein the fluid flows into the balloon from a time when introducing the fluid at the low temperature begins to a time when the laser beam is switched-off,
  heating the fluid before the fluid is introduced into the balloon by supplying energy to the heat-generating member during a time when a portion of the diseased tissue is heated to a temperature level which is effective for the treatment of the portion of the diseased tissue, and is lower than the temperature at which the living organ is damaged,
  detecting the pressure in the balloon to control the pressure in the balloon as the balloon is expanded by applying pressure with an adjustment of degrees of opening of the fluid inlet and the fluid outlet, or the pressure of the introduced fluid, whereby a stenosis portion of the living organ is expanded while the pressure in the balloon is controlled,
  switching-off the energy and
  cooling the portion of the diseased tissue below the temperature at which the living organ is not damaged.

11. A method for treating a patient which comprises the steps of:
  inserting the balloon catheter according to claim 1 into a living organ of a patient,
  introducing the fluid at a low temperature from the fluid inlet, and the fluid flows through the inside of the balloon and is discharged from the fluid outlet, wherein the fluid flows into the balloon from a time when introducing the fluid at the low temperature begins to after a time when the laser beam is switched-off,
  heating the fluid before the fluid is introduced into the balloon to heat a portion of a diseased tissue of the living organ from a range of 35 to 40° C. to a range of 60 to 80° C. within 30 seconds, by supplying energy to the heat-generating member, expanding the portion of the diseased tissue by applying a pressure of 500 kPa or smaller to the balloon, switching off the energy and cooling the portion of the diseased tissue from the temperature attained by the heating to a temperature of 45° C. or lower within 40 seconds.

12. A balloon catheter according to claim 1, wherein the heat-generating member is a metal member.

13. A balloon catheter according to claim 12, wherein the metal member is selected from the group consisting of stainless steel, chromium steel, ferrite steel and a nickel/titanium ultra-elastic alloy.

14. A balloon catheter according to claim 13, wherein the heat-generating member has a shape of a blade, a coil, a net, a braid or wool.

15. A balloon catheter according to claim 1, wherein the heat-generating member is disposed inside the lumen for introducing the fluid into the balloon in a distal portion of the catheter shaft.

16. A balloon catheter according to claim 1, wherein the heat-generating member is obtained by forming a portion of the lumen for introducing the fluid into the balloon at a distal portion of the catheter shaft into the heat-generating member.

17. A balloon catheter according to claim 16, wherein the lumen for introducing the fluid into the balloon comprises a metal braid in a polymer tubing and includes a portion for introducing the fluid into the balloon at a distal portion of the catheter shaft into the heat-generating member, said portion of the lumen being formed by removing a portion of the polymer tubing at a discharging end of the lumen to expose the metal braid.

18. A balloon catheter according to claim 1, wherein the heat-generating member is disposed at the outside of a discharging end of the lumen for introducing the fluid into the balloon in a distal portion of the catheter shaft.

19. A balloon catheter according to claim 1, wherein the balloon is made from a thermoplastic resin.

* * * * *